United States Patent
Angelides et al.

(10) Patent No.: US 10,825,550 B2
(45) Date of Patent: Nov. 3, 2020

(54) FECAL SAMPLE, BREATH SAMPLE COLLECTION AND ANALYSIS FOR TREATING INFLAMMATORY BOWEL DISEASE

(71) Applicant: Vivante Health, Inc., Houston, TX (US)

(72) Inventors: Kimon Angelides, Houston, TX (US); Eric Mirabel, Houston, TX (US)

(73) Assignee: Vivante Health, Inc., Houston, TX (US)

( * ) Notice: Subject to any disclaimer, the term of this patent is extended or adjusted under 35 U.S.C. 154(b) by 0 days.

(21) Appl. No.: 16/735,734

(22) Filed: Jan. 7, 2020

(65) Prior Publication Data

US 2020/0273540 A1 Aug. 27, 2020

Related U.S. Application Data

(60) Provisional application No. 62/811,429, filed on Feb. 27, 2019.

(51) Int. Cl.
*G16B 25/10* (2019.01)
*G16H 20/60* (2018.01)

(52) U.S. Cl.
CPC ............ *G16B 25/10* (2019.02); *G16H 20/60* (2018.01)

(58) Field of Classification Search
None
See application file for complete search history.

(56) References Cited

U.S. PATENT DOCUMENTS

| | | | | |
|---|---|---|---|---|
| 8,933,292 | B2 * | 1/2015 | Abraham | G16H 40/63 604/361 |
| 10,587,545 | B1 | 3/2020 | Bitoun et al. | |
| 2011/0192213 | A1 * | 8/2011 | Zimmerman | A01K 5/0225 73/23.3 |
| 2014/0148357 | A1 * | 5/2014 | Aune | C12Q 1/6883 506/9 |
| 2015/0313534 | A1 | 11/2015 | Angelides | |
| 2015/0317913 | A1 | 11/2015 | Angelides | |
| 2016/0097761 | A1 * | 4/2016 | Sano | G01N 33/497 73/23.3 |
| 2017/0076630 | A1 | 3/2017 | Angelides | |
| 2018/0119973 | A1 * | 5/2018 | Rothman | G05B 15/02 |
| 2020/0015707 | A1 * | 1/2020 | Ratto | A61B 5/742 |

OTHER PUBLICATIONS

Binder, Henry J. "Causes of chronic diarrhea." New England Journal of Medicine 355.3 (2006): 236.*
Suares, Nicole C., and Alexander C. Ford. "Diagnosis and treatment of irritable bowel syndrome." Discovery medicine 11.60 (2011): 425-433.*
Chandar, Apoorva Krishna. "Diagnosis and treatment of irritable bowel syndrome with predominant constipation in the primary-care setting: focus on linaclotide." International journal of general medicine 10 (2017): 385.*

* cited by examiner

*Primary Examiner* — G Steven Vanni
(74) *Attorney, Agent, or Firm* — Eric P. Mirabel

(57) ABSTRACT

The invention is related to a system for treating irritable bowel syndrome, Crohn's disease, ulcerative colitis (collectively, inflammatory bowel disease, or "IBD") by determining a number of indicators, including genetic markers, gene expression levels, levels of certain compounds in the gut or feces, hydrogen and/or methane levels, and concentrations of particular bacteria in the gut or feces, and correlating one or more such indicators with symptoms in test subjects with IBD; and correlating diet, drugs, supplements or other therapy, with alleviation of IBD symptoms. The correlations established in the test subjects are confirmed or refuted for individuals suffering IBD, and the treatments established as reducing symptoms are supported through messaging and compliance is verified by monitoring the indicators.

20 Claims, 10 Drawing Sheets

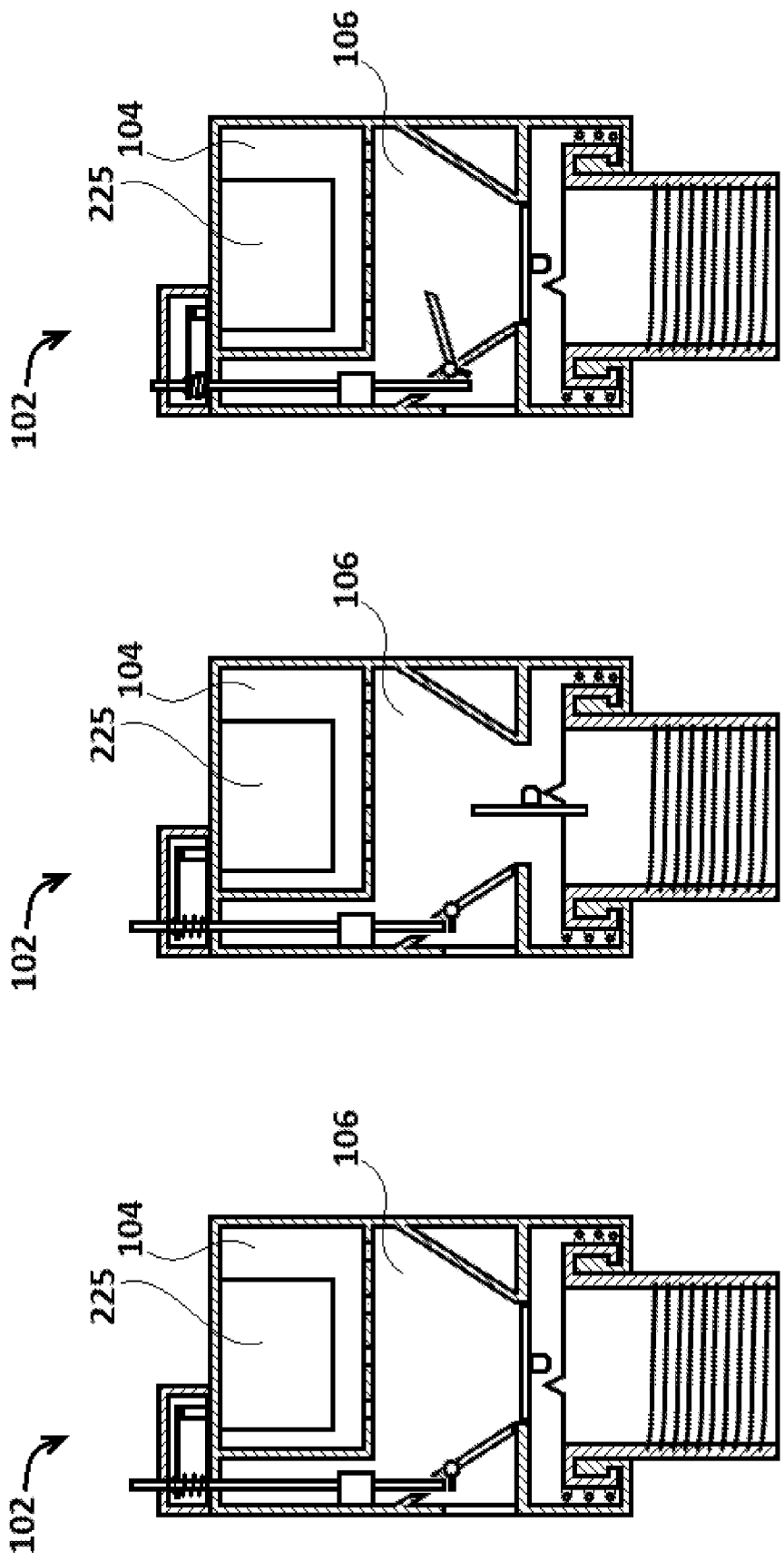

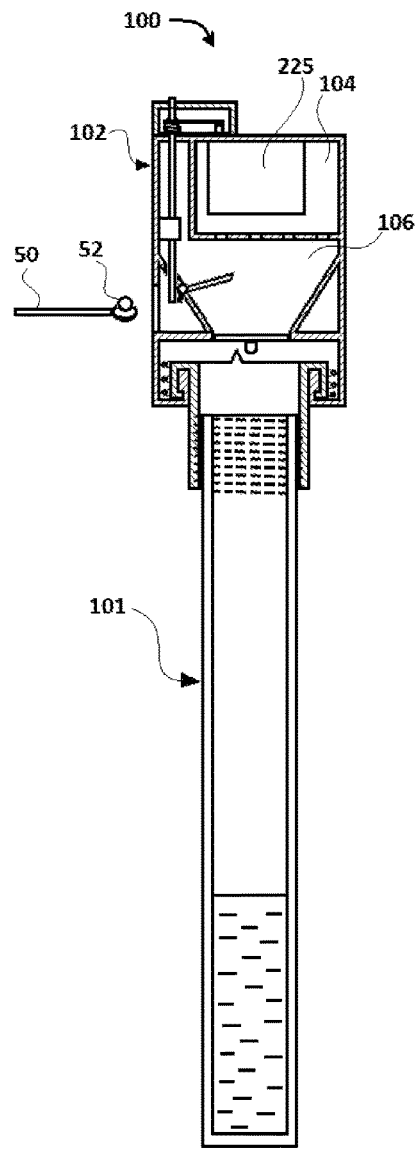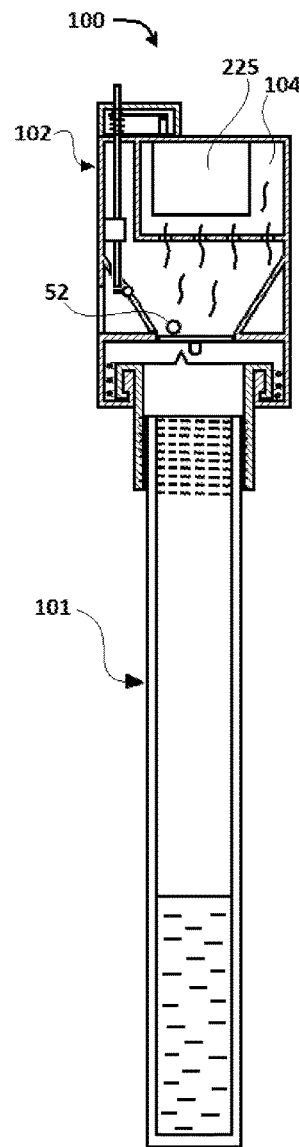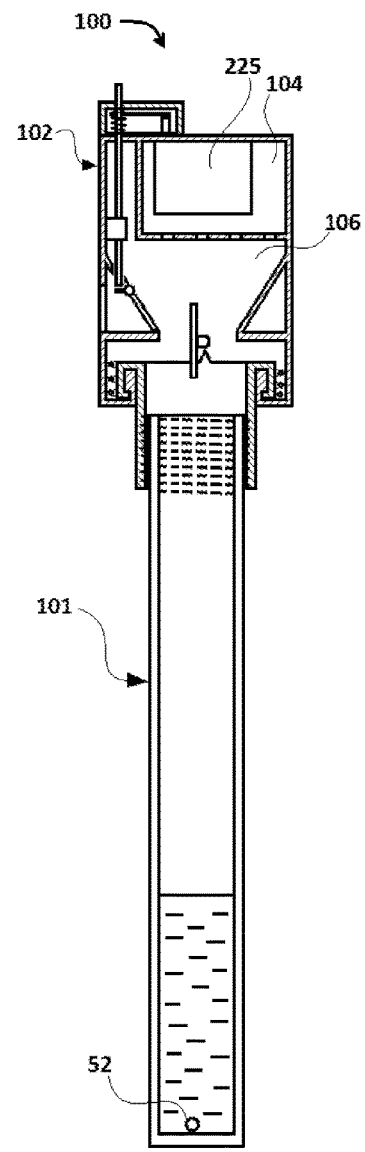

For Test Subjects:

For Individual X:

FECAL SAMPLE, BREATH SAMPLE COLLECTION AND ANALYSIS FOR TREATING INFLAMMATORY BOWEL DISEASE

BACKGROUND OF THE INVENTION

As much as 74% of the American population experiences various digestive problems and/or conditions. Chronic digestive diseases (such as celiac disease, Crohns disease, irritable bowel syndrome, or ulcerative colitis) affect at least 70 million people. Furthermore, up to 37% of patients with chronic digestive disease are admitted into an emergency room every year and 70% of such patients need some type of surgical intervention.

Making wise dietary choices can be confusing, particularly if certain foods, stress, and/or exercise exacerbate the problem. For individuals with chronic digestive complications or discomfort making everyday food choices, can be confusing, unpredictable, and often embarrassing (in the case of inadvertent public gas or stool discharge). Medical regimens to address these diseases and assist in relieving symptoms are complicated and involve complicated medication regimens that are difficult and expensive to manage. Changes in diet can ameliorate or sometimes even eliminate the symptoms of these conditions. Methane and hydrogen production can be used as markers to determine the effect of dietary changes on symptoms. Symptom relief has been achieved with a low-FODMAP diet (low in fermentable sugars) in a large majority of functional gastrointestinal disorders patients with fructose or lactose intolerance. Wilder-Smith et al., "Predictors of response to a low-FODMAP diet in patients with functional gastrointestinal disorders and lactose or fructose intolerance." Aliment Pharmacol Ther 2017 April; 45(8):1094-1106.

Animal model experiments have shown that methane, a gaseous by-product of intestinal bacteria, slows small intestinal transit and appears to do so by augmenting small bowel contractile activity. Pimentel M, et al., "Methane, a gas produced by enteric bacteria, slows intestinal transit and augments small intestinal contractile activity." Am J Physiol Gastrointest Liver Physiol 2006; 290: G1089-95. In the lactulose breath test (where the patient is challenged with lactulose and then methane production is measured), methane in the breath of IBS patients has been associated with severity of constipation. Chatterjee S, "The degree of breath methane production in IBS correlates with the severity of constipation." Am J Gastroenterol 2007; 102: 837-41. Elevated hydrogen production, as measured in the breath, is also widely believed to be associated with symptoms in inflammatory bowel disease.

The levels of certain volatile organic metabolites in the feces of patients with diarrhea-predominant IBS (IBS-D), active Crohn's disease (CD), ulcerative colitis (UC) (collectively, inflammatory bowel disease, or "IBD") and healthy controls are indicators of IBD. Ahmed, I. et al. "An Investigation of Fecal Volatile Organic Metabolites in Irritable Bowel Syndrome," PLoS One. 2013; 8(3): e58204. These researchers arrived at a list of 28 such volatile metabolites associated with IBS and not healthy controls, and a list of 11 such volatile metabolites associated with healthy controls and not with IBS.

TABLE A

| No. | Compounds |
|---|---|
| 1 | Butanoic acid, ethyl ester |
| 2 | Propanoic acid, methyl ester |
| 3 | 1-Methyl-2-(1-methylethyl)-benzene |
| 4 | Butanoic acid, butyl ester |
| 5 | Butanoic acid, propyl ester |
| 6 | Hexanoic acid, methyl ester |
| 7 | Propanoic acid, propyl ester |
| 8 | Acetic acid, butyl ester |
| 9 | Butanoic acid, 3-methyl-, butyl ester |
| 10 | Propanoic acid, butyl ester |
| 11 | Cyclohexanecarboxylic acid, ethyl ester |
| 12 | Butanoic acid, 2-methyl-, propyl ester |
| 13 | Ethanoic acid, ethyl ester |
| 14 | Pentanoic acid, 4-methyl |
| 15 | Acetic acid, pentyl ester |
| 16 | Pentanoic acid, butyl ester |
| 17 | Butanoic acid, 3-methyl-, propyl ester |
| 18 | Cyclohexanecarboxylic acid, propyl ester |
| 19 | 6-Methyl-5-hepten-2-one |
| 20 | Propanoic acid, 3-methyl-butyl ester |
| 21 | Ethanoic acid, 3-methyl-l-butyl ester |
| 22 | Cyclohexanecarboxylic acid, butyl ester |
| 23 | Benzoic acid, 2-hydroxy-, methyl ester |
| 24 | Pentanoic acid, 4-methyl-, pentyl ester |
| 25 | Butanoic acid, 3-methyl-, methyl ester |
| 26 | Thiopivalic acid |
| 27 | 5-Methyl-2-(1-methylethyl)-cyclohexanone |
| 28 | 4-Methyl-1-Indole |

TABLE B

| | |
|---|---|
| 1 | 2-Heptanone |
| 2 | 2-Methylpropanal |
| 3 | 3-Methylbutanoic acid |
| 4 | Undecane |
| 5 | 3-Methylbutanal |
| 6 | 2-Methylpropanoic acid |
| 7 | 2-Methyl-l-propanol |
| 8 | 1R-a-Pinene |
| 9 | 2-Penhifizran |
| 10 | Methoxy-phenyl-oxime |
| 11 | 2-Methylfuran |

These compounds could be detected in a fecal sample to indicate the presence of IBD, or the likelihood that it is in remission or symptoms have alleviated (where the compounds in Table B predominate). More importantly, they could be used to determine an appropriate diet for amelioration of IBD, by determining which foods cause increases or decreases in these volatile metabolites, first in a group of test subjects using AI/software agents to find the optimal foods, then in each individual who would be a participant, who could be monitored for these metabolites, and would report their diet on a regular basis. With that information for the individual the software agent would determine the optimal diet to ameliorate IBD for the individual.

SUMMARY OF THE INVENTION

The invention includes finding correlations, in patient feces, between certain genetic markers indicative of mutant subspecies of the bacteria in the gut, certain levels of gene expression, certain levels of volatile organic compounds (VOCs) and certain levels of methane and hydrogen in patient breath (or feces), certain levels of gut bacteria making up the microbiome; and negative symptomology ("Events"), as determined in a group of test subjects. It further includes finding foods which prevent, reduce incidence of or otherwise ameliorate Events, and finding in test subjects correlations between consuming such foods and levels (i) of volatile organic compounds (VOCs) in patient feces, and levels (ii) of methane and hydrogen in patient breath (or feces), and optionally, (iii) microbiome composition (including as determined from fecal genetic markers indicating mutants or wild type, analyzed by either DNA or 16 S RNA analysis), or (iv) gene expression; so that levels (i), (ii), (iii) and/or (iv) can serve as indicators of a diet which reduces Events. As a further step, the molecular-level microbiome analysis can identify changes in gut bacteria over time, and correlate those changes with changes in levels (i) or (ii) above, and with symptom relief. Thus, mutant bacteria associated with symptoms can be identified from fecal samples.

It further includes finding a diet which ameliorates Events in test subjects with genetic markers or levels of gene expression correlated with IBD; and then applying that diet to participants with the same markers or gene expression levels.

After finding such an optimal diet for the test subjects, the diet is tried in an individual, and changed as necessary to reduce Events and/or change levels (i), (ii), (iii) and/or (iv) to more desirable levels—with the goal being to prevent, reduce incidence of or ameliorate Events in the individual.

Test subjects and participants send in fecal samples preferably collected with a collection system as outlined in FIGS. 1-4C; or otherwise, for testing for levels (i), (ii), (iii) and/or (iv). For preferably determining levels of (ii), test subjects and participants periodically measure methane and hydrogen in the breath, using a wireless device which sends the results to a server. See e.g., US Publ'n No. 20180271404 (disclosing a methane and hydrogen sensor for breath, to integrate with a smartphone or other device). Test subjects and participants report their symptoms and food intake, preferably using a wireless device which sends the results to the server. Alternatively, the off-gassed methane and hydrogen in a fecal sample can be measured.

The server includes software agents which analyze the input from test subjects and participants against a profile they initially provided, and sends messages regarding foods to avoid or preferentially consume, based on all the available information. The software agents preferably monitor the effect of particular messages on particular test subjects or participants, in terms of moving their food consumption to one which is more preferred, and sends the more effective messages going forward to those. The server preferentially also determines if participants are accurately reporting their food consumption, by monitoring the reported food consumption against levels (i), (ii), (iii) and/or (iv), and determining if there is the predicted correlation. If the predicted correlation is lacking, the participant is assumed to not be accurately reporting food consumption; and can be sent a message to report more accurately.

Fecal samples must be initially monitored for markers and gene expression levels, and baseline VOCs. Initial breath samples are monitored for methane and hydrogen levels. Fecal samples are then periodically monitored for changes to genetic markers, gene expression levels, baseline VOCs, and breath samples are periodically monitored for methane and hydrogen levels. A preferred sample collection system includes a disposable feces catcher to place below the toilet seat, and a sealed, pre-addressed sample collection tube, which has a self-sealing cap through which a probe with sample adhered at one end, is pushed into the interior of the tube.

An alternative fecal sample container has a multi-chamber design and can be used to determine the quantity of hydrogen and/or methane from a fecal sample, instead of or in addition to the measurement of hydrogen and/or methane from the subject's breath. In this alternative, a relatively standard amount of fecal material is placed in the container and the off gas is collected—preferably in a chamber of the same sample container. The off gas can also be analyzed to determine the levels of VOCs in the fecal sample.

The foregoing has outlined rather broadly several aspects of the present invention in order that the detailed description that follows may be better understood.

BRIEF DESCRIPTION OF THE DRAWINGS

FIG. 3A is a sectional view of the upper part of the assembled fecal sample container taken along a vertical plane with the fecal port and port control in closed position and the lower gate in chamber 106 closed.

FIG. 3B is a sectional view of the upper part of the assembled fecal sample container taken along a vertical plane with the fecal port and port control in closed position and the lower gate in chamber 106 open.

FIG. 3C is a sectional view of the upper part of the assembled fecal sample container taken along a vertical plane with the fecal port and port control in open position and the lower gate in chamber 106 closed.

FIG. 4A is a sectional view of the fecal sample container taken along a vertical plane with the fecal port and port control in open position and the lower gate in chamber 106 closed.

FIG. 4B is a sectional view of the fecal sample container taken along a vertical plane with the fecal port and port control in closed position, a fecal sample in place in chamber 106, and the lower gate in chamber 106 closed.

FIG. 4C is a sectional view of the fecal sample container taken along a vertical plane with the fecal port and port control in closed position, and the lower gate in chamber 106 open, allowing the fecal sample to fall into the tube 101.

For a more complete understanding of the present invention, and the advantages thereof, reference is now made to the following description in conjunction with the accompanying drawings, outlined above. stop

DETAILED DESCRIPTION

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in Value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the term "comprising," when utilized, means "including, but not necessarily limited to"; it specifically indicates open-ended inclusion or membership in the so-described combination, group, series and the like.

It is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in any appropriately detailed structure.

Embodiments of the invention are related to a system providing a hydrogen and/or methane sensor device and a wireless platform in communication with the sensor device to periodically analyze the hydrogen and/or methane off gassing of an IBD subject's breath (or from feces) and correlating the levels of hydrogen and/or methane with symptoms or Events.

Figure 1:
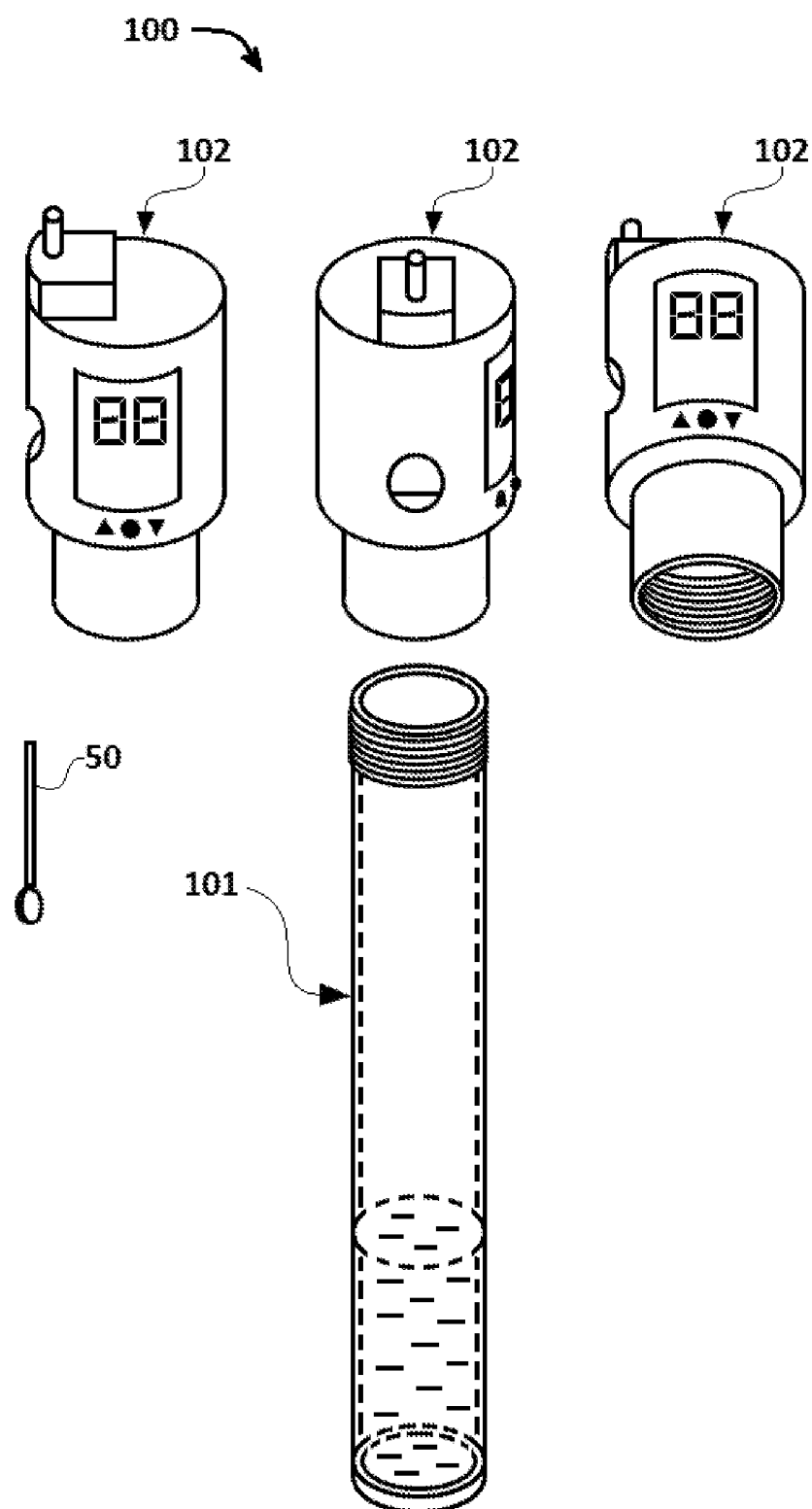
FIG. 1 is an exploded view of components of a fecal sample container and other components of a fecal sampling kit.
Figure 2:
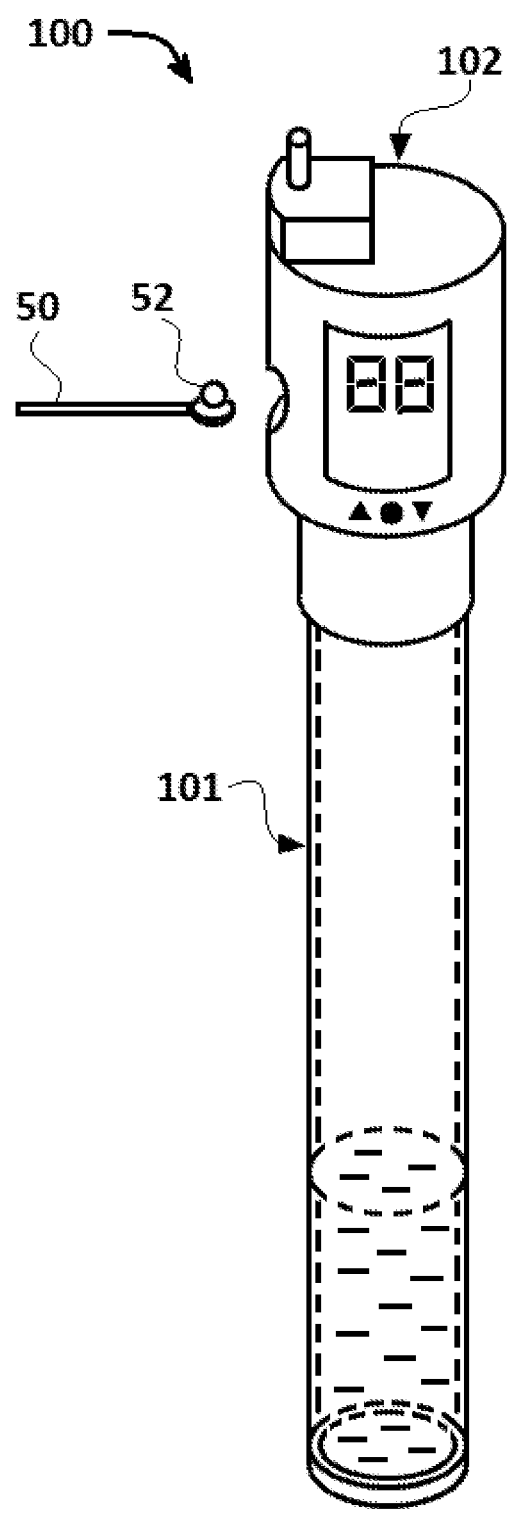
FIG. 2 is an assembled fecal sample container of the components shown in FIG. 1, with a fecal sample outside.

Referring to FIG. 1, it shows a fecal sampling kit 100 with a spatula 50 and a fecal sample container 101. Spatula 50 can be used by the subject to scoop a small measured amount of fecal matter into chamber 106. As noted in the Summary, hydrogen and/or methane is preferentially measured from the subject's breath, using a device as described in US Publ'n No. 20180271404. But it could also be measured from a fecal sample, where a relatively standard volume of fecal material 52 is placed in chamber 106, and the off gassed hydrogen or methane is measured.

Referring to FIGS. 3A to 4C, fecal sample container 101 has a threaded cap 102 with two chambers, 104, 106, each of which is sealed but can be accessed by spatula, 50, carrying a solid, like fecal sample 52. Upper chamber 104 is sealed from the environment and capable of collecting gases from a sample 52 in the cap's lower chamber 106. The lower trap door of the lower chamber 106 is opened by e.g., twisting the cap 102 to allow sample 52 therein to fall into container 101. An automatic timer 225 in cap 102 is activated by a sensor, which detects when the port on the side of chamber 106 is opened for the sample to enter. The automatic timer 225 is preferably set to limit the gas measurement by a gas sensor (now shown) for a specific period of time (e.g., 10 seconds, 20 seconds). Several off gassed hydrogen/methane measurements are taken in succession and stored as individual values specific for a particular fecal sample of the individual subject. In one embodiment, all measurement values and related subject information for a specific fecal sample are recorded and then transferred to a data processor, preferably wirelessly, such as by Bluetooth to a mobile phone or other wireless device. One preferred method for measuring the hydrogen/methane in a fecal sample, is to include a tube running from upper chamber 104 and detachably connecting to the breath sampler device (as described in US Publ'n No. 20180271404), which then measures the levels of hydrogen/methane in the fecal sample from the gas level in chamber 104.

After cap 102 is manipulated to open the lower chamber 106, the lower trap door in chamber 106 opens and fecal sample 52 falls into container 101. Cap 102 is twisted again to seal sample 52 in container 101. Container 101 is then shipped for fecal sample analysis and/or optionally methane and hydrogen gas analysis, or, optionally VOC analysis, of the gas collected in the upper chamber 104. Optionally the fecal sampling kit 100 may also contain a sealable impermeable pre-addressed bag that the fecal sample container 101 is placed into for mailing to a laboratory for analysis. The fecal sample 52 analysis can be for levels of the compounds in Tables A and B above, genetic markers associated with IBD, levels of gene expression correlating with IBD, and the bacterial composition of the sample.

A personalized database for subjects is created by capturing data from multiple sources, including medical records such as their medical history, laboratory data, diagnoses, treatment plans, and family medical history. Another example of such data is data measured by one or more biodata or sensor devices. Biodata can be collected by devices equipped with the necessary software to process the data generated by the device and to communicate the collected data to the personalized database and from there, to a processor. Examples of such biodata-collecting devices include glucometers, hydrogen or methane sensors, temperature sensors, heart rate monitors, blood pressure monitors, and activity sensors with tri-axis or multi-axis accelerometer chips.

The personalized database will also include input from extensive questionnaires and individualized insights gained by understanding the subject's social structure, daily routines and cultural background to assist in understanding how that person copes with a chronic condition or symptoms on a daily basis. This type of data is vital to finding personalized treatment plans that a person will adhere to and that will provide positive changes in a person's quality of life. Although people share the same disease or the same chronic symptomology, their ability to navigate through the symptoms often will include personal adjustments to their daily routines. Many people facing chronic diseases and associated uncomfortable or embarrassing symptoms will try alternative approaches that they are unwilling to share with their physicians. Thus, a great deal of relevant information does not appear in their medical records. Often these alternative approaches will include herbal remedies, supplements, acupuncture or acupressure, reflexology, relaxation techniques, or exercise regimes such as yoga or stretching.

A processor stores a number of software applications and agents executable by the processing unit. The software applications and agents include a data extraction and analysis application that extracts, identifies and links associated processed data acquired from various sources. The data extraction applications include inference engines and other algorithmically based applications used to identify and correlate relevant information in a personalized database and external data sources. The processor, through agents and applications, is capable of performing all the operations described in the flowcharts in FIGS. 5A to 7B.

In one embodiment, the processor can include a processing unit having a multitude of interrelated elements. Embodiments of the processing unit can be implemented to some extent as software modules installed and running on one or more processing systems, such as servers, workstations, tablet computers, PCs, and so on. The processor generally includes a knowledge module that derives further knowledge or informational data from existing knowledge using inference, analysis, crowd sourced wisdom and continuous monitoring data from a personalized database of the subject.

Thus, the knowledge module is a "care" analysis engine that stores its data in the data repository. The data repository can include one or more databases that communicate with the knowledge module. The knowledge module can also receive data from an external data sourced database. The external sourced database may include data from various sources, such as laboratories, insurance companies, hospitals/clinics. media companies, 24/7 call centers/caregivers, account administrators, and other sources. The data from the external database can be extracted and transferred to the knowledge module using dynamic APIs.

The processor processes information accessed and derived by the knowledge module to determine personalized clinical and nutritional decision analytics for subjects or individual system participants. The processor may include one or more algorithms that provide both content and personalized rules to provide feedback to the user in real time. For example, the processor may include code for predicting trends based upon the subject's personalized health profile and preferences. The information acquired from a subject's personalized data input by the subject and data derived from an analysis of subject samples may be stored in the data repository and accessed by the processor.

The data extraction applications on the processor identify, analyze and correlate relevant information in the personalized database and data continuously gathered, including hydrogen and methane levels (sourced from breath or fecal off-gas), the genetic marker and/or gene expression analysis, the analysis of the VOCs in patient feces; and, as input by the subject: the diet and foods consumed and the adverse events (symptoms of IBD). See FIGS. 5A-6B. The data continuously gathered can also include gut bacterial composition. See FIGS. 7A, 7B.

The processor includes applications/agents which, based on the analysis of the personalized database and the data continuously gathered, send messages to subjects regarding food consumption; particularly, how to better conform to a low FODMAP or other preferred diet. The processor may also message daily meal, an activity plan or exercise plan for the subject, recommendation to contacting a coach or health guide (a Health Sherpa), nutritional guidance, subject reports and predictions, subject health profiles and videos or chat sessions.

Typically, the processor will include code for predicting trends based upon the individual subject's personalized health profile and preferences. For example, the rules may pertain to a daily meal or activity plan for the participant based on personal preferences, a matching of the subject to one or more health consultants, nutrition guidance, exercise routines, general health predictions and alerts, trends and improvements in the subject's health profile and video/chat sessions. Various parameters are considered in determining recommendations, educational messages, and directives to the subject. The processor analyzes and correlates the relevant data to determine useful information for the specific subject and transmits that information to the subject, including information relating to nutrition, exercise advice and treatment. Access privileges to any processor information may also be driven rules based on health care privacy regulations and laws.

A portal on the processor, which is preferably web-based, can be provided by the processor. The portal can provide interfaces for reporting and displaying the data analyzed by the processor, and including information and recommendations for the subject or the health care personnel, or messaging for the subject. Portal access is controlled through established access privileges.

To use the care management system of the invention, the subject uses fecal sampling kit 100 and preferably, also a breath sampling unit. The subject will collect a fecal sample 52 using a spatula 50 and place it into fecal sample container 101. The subject will then either follow the procedure to use the cap system to measure hydrogen and methane from the sample, or use the breath sensor in the alternative. The gas measurements are then communicated to the processor, and the fecal sample container is sealed and sent for genetic and VOC analysis, and optionally, for bacterial composition.

The processor's software agents analyzes and correlates all analysis including those input to the personalized database, to enhance the ability of the care management system to provide updated and relevant guidance, through messaging to the subject. For example, the software agents will correlate changes in incidence of symptomatic events with levels of methane and hydrogen, VOCs, genetic markers and gene expression, as well as diet, and optionally, the feces bacterial composition. The specifics of these correlations and analysis are illustrated in FIGS. 5A-7B.

Another use for the analyses set forth in FIGS. 5A-7B, other than optimizing diet as illustrated, is to determine effectiveness and dosage of therapeutic drugs on the subject. The same analysis can be used as for diet optimization, to find drugs and dosages which effectively reduce symptomatic events ("Events" in FIGS. 5A-7B).

Figure 5A:
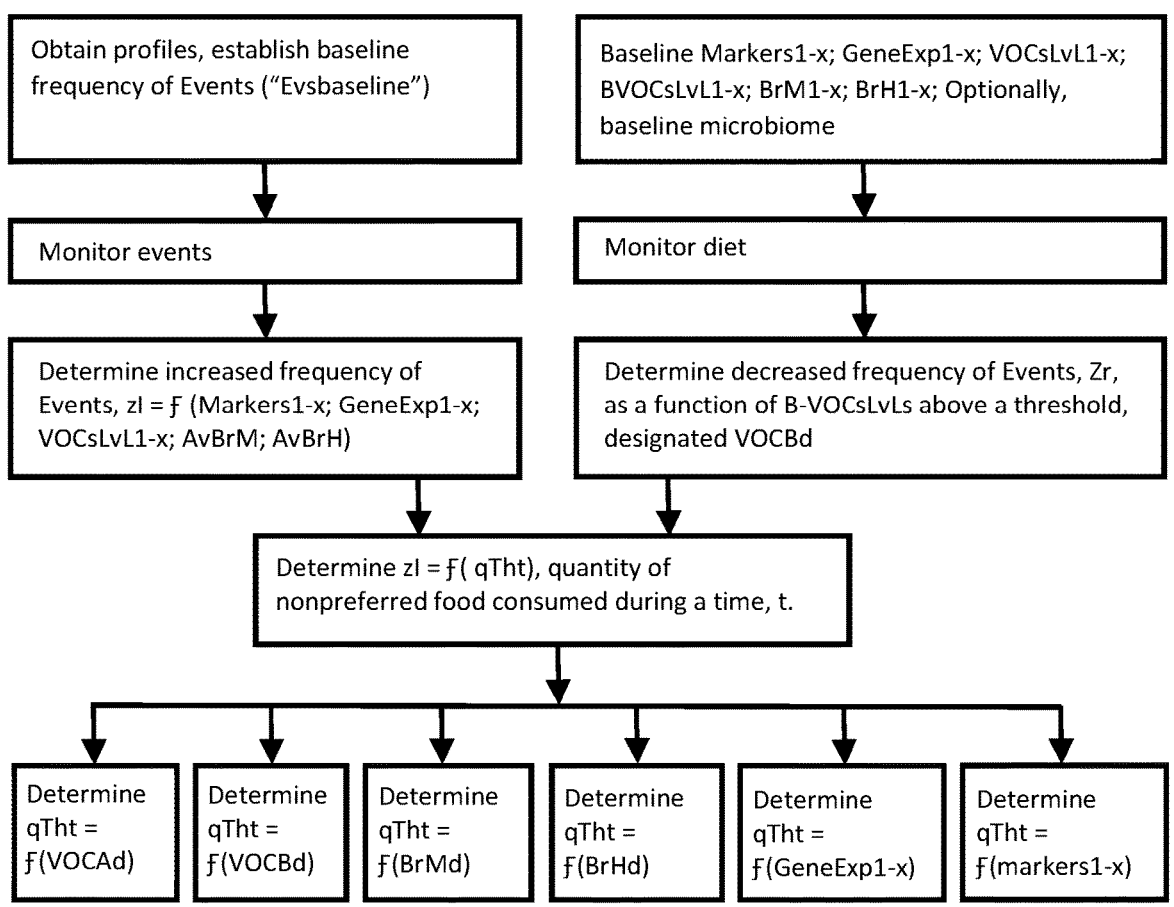
FIG. 5A, 5B are two successive pages of a flow chart showing a method for determining correlations between (independent variables) certain genetic markers, gene expression levels, volatile organic compound levels, and hydrogen and methane levels in the breath (or feces), to both adverse events and diet, for IBD patients. It further shows how to confirm the correlation for an individual with IBD, and messaging that individual to adhere to a recommended diet, and optionally, messaging the individual to report the diet accurately (if the data and analysis indicates it is not reported accurately).
Figure 5B:
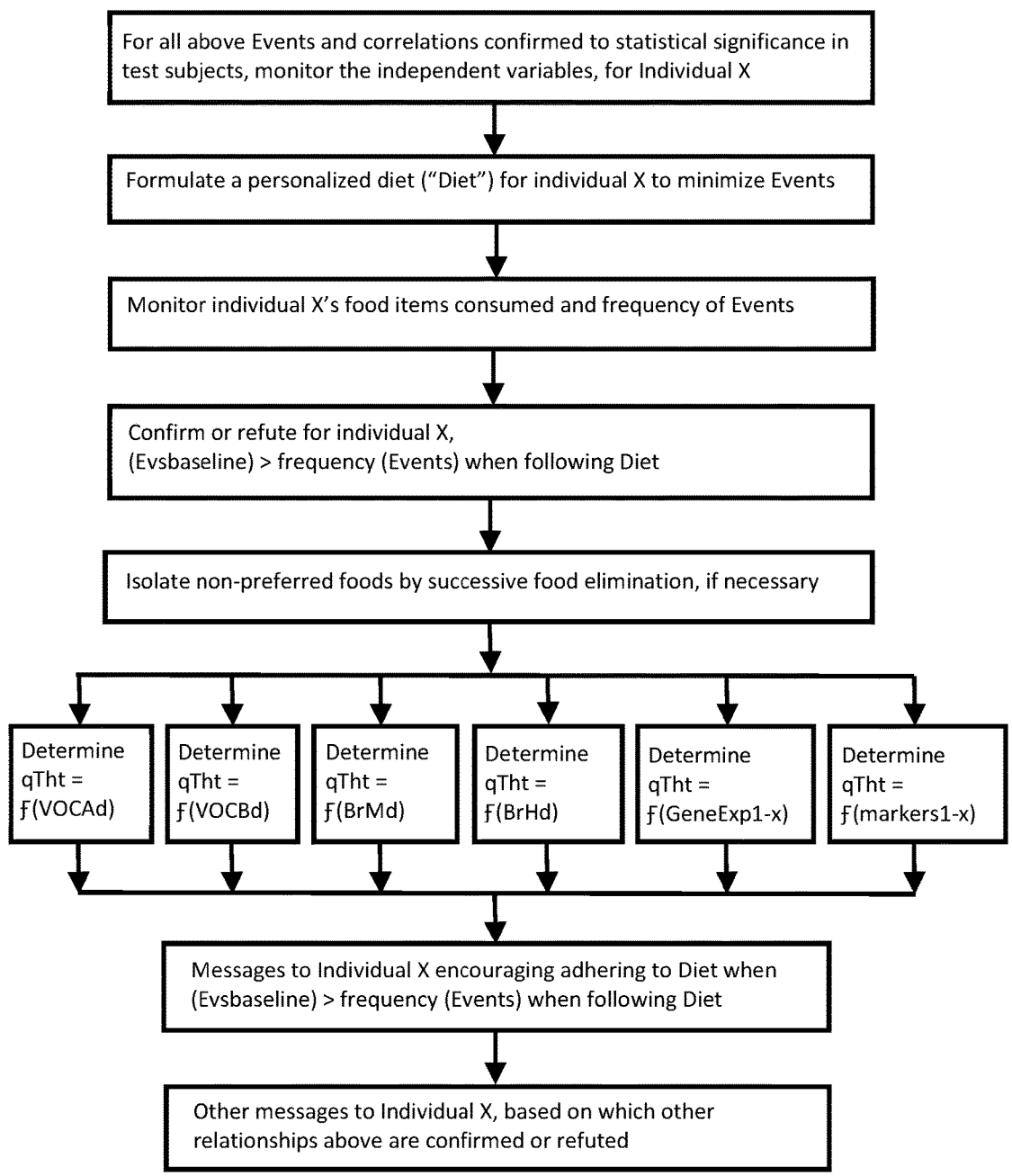

Referring to FIGS. 5A, 5B, where the steps are shown in flow chart form with limited explanation, the following steps 1 to 23 are a comprehensive explanation of the steps in the FIGS. 5A, 5B process.

1) Obtain details of digestive health of each test subject: health profiles, and past and present digestive ailments i.e.: whether suffering from IBS, IBD, frequent diarrhea, high frequency flatulence, high frequency bowel movements ("Events" or "symptoms"), and also the baseline frequency of Events ("Evsbaseline");

2) Perform baseline fecal sample collection for test subjects to initially determine: (i) DNA and/or RNA markers for wild type and mutant beneficial or detrimental bacterial strains in the gut microbiome ("Markers1-x"); (ii) gene expression of any candidate genes (from the individual or the microbiome bacteria) whose expression is elevated or decreased in the test subjects from normal ("GeneExp1-x"); (iii) levels of volatile organic compounds in Table A ("VOCsLvL1-x") and in Table B ("B-VOCsLvL1-x") associated with test subjects where the VOCsLvL and B-VOCsLvL can be measured from gas associated with the fecal sample; and (iv) determine from a breath sensor carried by test subjects the methane ("BrM") and hydrogen levels ("BrH") in each subjects' breath, where 1-x indicates a reading at a different time for methane and hydrogen levels, which can be transmitted to a server;

3) Monitor diet of each test subject using a wireless device which allows input of all food items and quantity consumed; with recommendations on screen for low FODMAP foods, and preferably showing carbohydrate content and glycemic Index, fat and protein content, gluten levels, for each meal or for each food item;

4) Monitor each test subject's frequency of Events using the wireless device, which allows their entry and category;

5) Collect fecal samples at intervals for each test subject: and monitor changes in Markers1-x; GeneExp1-x; VOCsLvL1-x; and B-VOCsLvL1-x; Optionally: BrM or BrH, preferably, determine the average of the readings ("AvBrM" and "AvBrH") during each collection period; (Optionally, monitor the methane ("M1-x") and hydrogen levels ("H1-x") in each subjects' fecal sample and use those measures for AvBrM and AvBrH, instead of measuring them from the subject's breath.)

6) Use a software agent to determine dependency of increased frequency of Events, zl (as the dependent variable), with the independent variables being: Markers1-x; GeneExp1-x; VOCsLvL1-x; AvBrM; AvBrH; wherein all independent variables are determined across all test subjects; using a software agent which (i) determines correlation of zl with each independent variable using a univariate hypothesis test, where the null hypothesis is "the presence of this marker, or this level of gene expression or greater, or this level of volatile organic compounds or greater, or these levels of hydrogen and methane or greater, are not associated with zl"; where such markers are designated Md, such gene expression levels are designated GEd, such levels of organic compounds are designated VOCAd; such average levels of methane are designated; BrMd, and such average levels of hydrogen are designated BrHd (ii) performs a multivariate regression model of all possible combinations of the independent variables Markers1-x; GeneExp1-x; and VOCsLvL1-x, AvBrM; AvBrH with substantially the same null hypothesis as in step (i) but where the word "or" is "and"; to represent the combination of independent variables modeled, where the following formula represents this multivariate regression model:

$zl = f(Markers1\text{-}x; GeneExp1\text{-}x; VOCsLvL1\text{-}x; AvBrM; AvBrH)$

Determine the independent variables and combinations thereof where the dependency of increased frequency of Events, zl, is established at a confidence interval (CI) of at least 95% for the appropriate null hypothesis noted above in steps (i) and (ii); for markers Md, for gene expression levels GEd, for levels of organic compounds VOCAd; for levels of methane AvBrM; and for levels of hydrogen AvBrH.

7) Use a software agent to determine dependency of increased frequency of Events, zl (as the dependent variable), with the dependent variable being a diet with consumption of a quantity, q, of FODMAP or other specified (non-preferred) foods above a threshold, Th, consumed in a period of time, t, as represented by the formula:

$zl = f(q(Th)(t))$, where such consumption is designated "qTht";

where the dependency of increased frequency of Events, zl, is established at a confidence interval (CI) of at least 95% (where the null hypothesis is: "consumption of a quantity, q, of FODMAP or other non-preferred foods above a threshold, Th, consumed in a period of time, t, are not associated with increased frequency of Events, z";

8) Use a software agent to determine dependency of decreased frequency of Events (as the dependent variable, Zr), with the independent variable being a level of volatile organic compounds in Table B ("B-VOCsLvL1-x") above a threshold associated with normal subjects or remission (see specification), where the B-VOCsLvL can be measured from gas associated with the fecal sample, and where such dependency is established at a confidence interval (CI) of at least 95% (where the null hypothesis is: "Levels of B-VOCsLvLs above this threshold are not associated with decreased frequency of Events, Zr"; where such levels are designated VOCBd), where the following formula represents this step 8:

$Zr = f(BVOCsLvL1\text{-}x)$

9) Use a software agent to determine correlation between consumption of qTht and levels of VOCBd (below the threshold):

$qTht = f(VOCBd)$ at a confidence interval (CI) of at least 95%, by using as a null hypothesis: "consumption of qTht does not correlate with levels of VOCBd below the threshold."

10) Use a software agent to determine correlation between consumption of qTht and levels of VOCAd (above the threshold):

$qTht = f(VOCAd)$ at a confidence interval (CI) of at least 95%, by using as a null hypothesis: "consumption primarily of qTht does not correlate with levels of VOCAd above the threshold."

11) Use a software agent to determine correlation between consumption of qTht and levels of methane BrMd (above the threshold):

$qTht = f(BrMd)$ at a confidence interval (CI) of at least 95%, by using as a null hypothesis: "consumption primarily of qTht does not correlate with levels of BrMd above the threshold."

12) Use a software agent to determine correlation between consumption of qTht and levels of hydrogen BrHd (above the threshold):

$qTht = f(BrHd)$ at a confidence interval (CI) of at least 95%, by using as a null hypothesis: "consumption primarily of qTht does not correlate with levels of BrHd above the threshold."

13) Based on an individual X's profile including dietary restrictions, and the diet determined in steps 7 and 9 to minimize Events, formulate a personalized diet ("Diet") for individual X to minimize Events in view of the individual X profile and dietary restrictions, and provide the Diet to individual X on the wireless device;

14) Monitor individual X's food items consumed and frequency of Events, based on entries in individual X's wireless device;

15) Confirm or refute for individual X correlation of Diet with decreased frequency of Events ("Zr") as compared with Evsbaseline; i.e., individual X following the Diet results in (Evsbaseline)>frequency (Events);

16) Confirm or refute for individual X, a decreased frequency of Events (Zr) as compared with Evsbaseline; for each of: gene expression levels<GEd, VOCsLvL<VOCAd, and B-VOCsLvL>VOCBd; AvBrM<BrMd; AvBrH<BrHd; and an increased frequency of Events (zl) as compared with Evsbaseline (i.e., frequency (Events)>(Evsbaseline)) with the presence of markers Md in the sample;

17) Confirm or refute for individual X that consumption of qTht correlates with levels of VOCAd (above the threshold) (Correlation A);

18) Confirm or refute for individual X that consumption of qTht correlates with levels of VOCBd (below the threshold) (Correlation B);

19) Confirm or refute for individual X that consumption of qTht correlates with levels of BrMd (above the threshold) (Correlation C);

20) Confirm or refute for individual X that consumption of qTht correlates with levels of BrHd (above the threshold) (Correlation D);

21) If individual X shows a decreased frequency of Events (Zr) where any of the following are true: VOCsLvL<VOCAd; B-VOCsLvL>VOCBd; AvBrM<BrMd; AvBrH<BrHd; and markers Md are absent; and if any of Correlations A through D are established for individual X, but individual X does not show decreased frequency of Events by following the Diet, message individual X to do one or more of: enter all food consumed, accurately report of food intake or do not enter foods erroneously; and if individual X continues to not show decreased frequency of Events by following the Diet, send messages to individual X to sequentially eliminate particular foods typically consumed until either all foods consumed are eliminated and deemed not causative, or foods associated with the failure to decrease frequency of Events zl are identified (i.e., which foods fail to alleviate symptoms); and 22) If individual X shows decreased frequency of Events when following the Diet, and shows increased frequency of Events when not following the Diet: message individual X about (i) the Diet and/or the importance of consistently following the Diet and (ii) specifying in the messages how to conform individual X's food intake to the Diet, based on the food intake reported by individual X during periods when there was increased frequency of Events (see flowchart B examples).

Figure 6A:
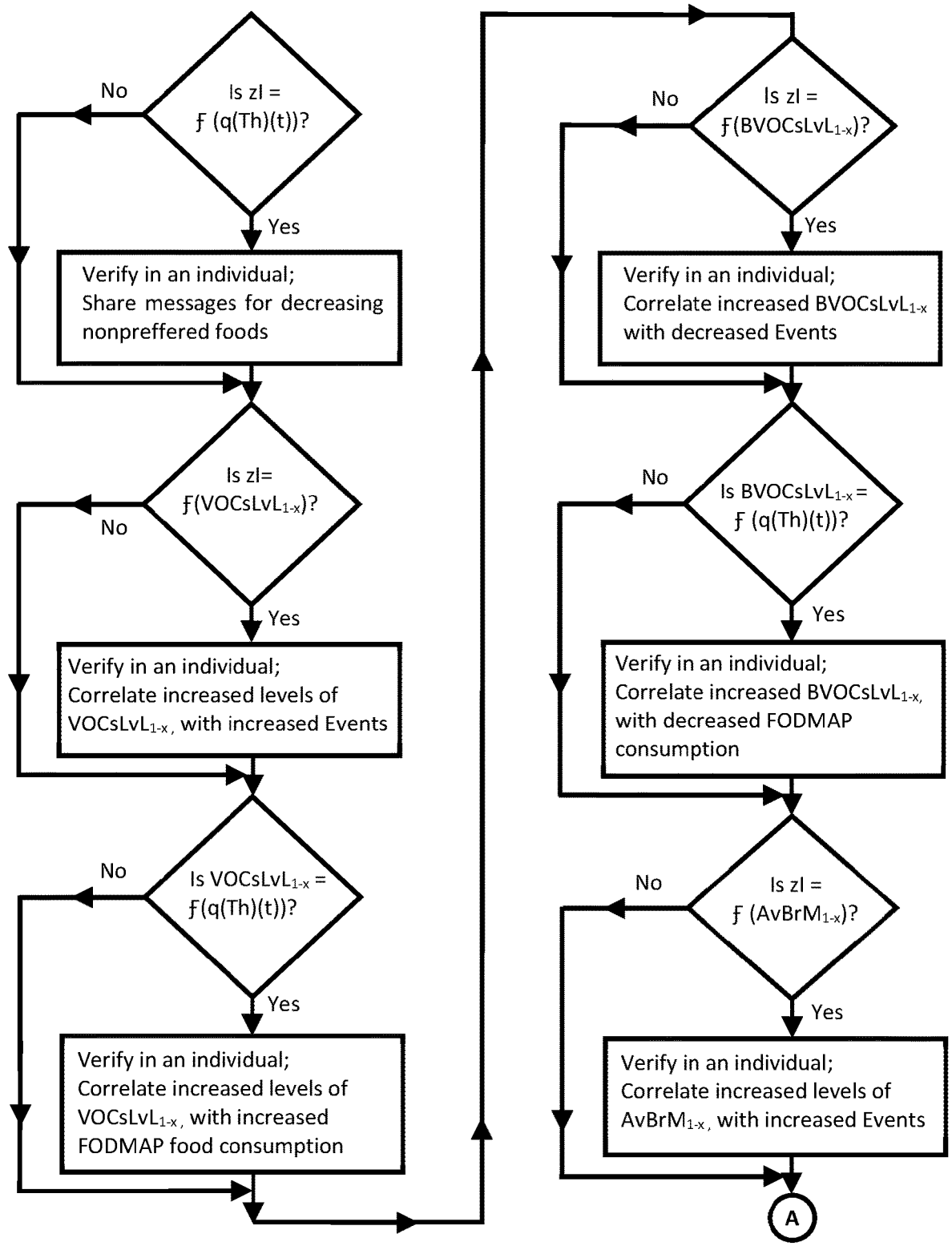
FIG. 6A, 6B show the equations representative of some of the steps in FIG. 5A, 5B.
Figure 6B:
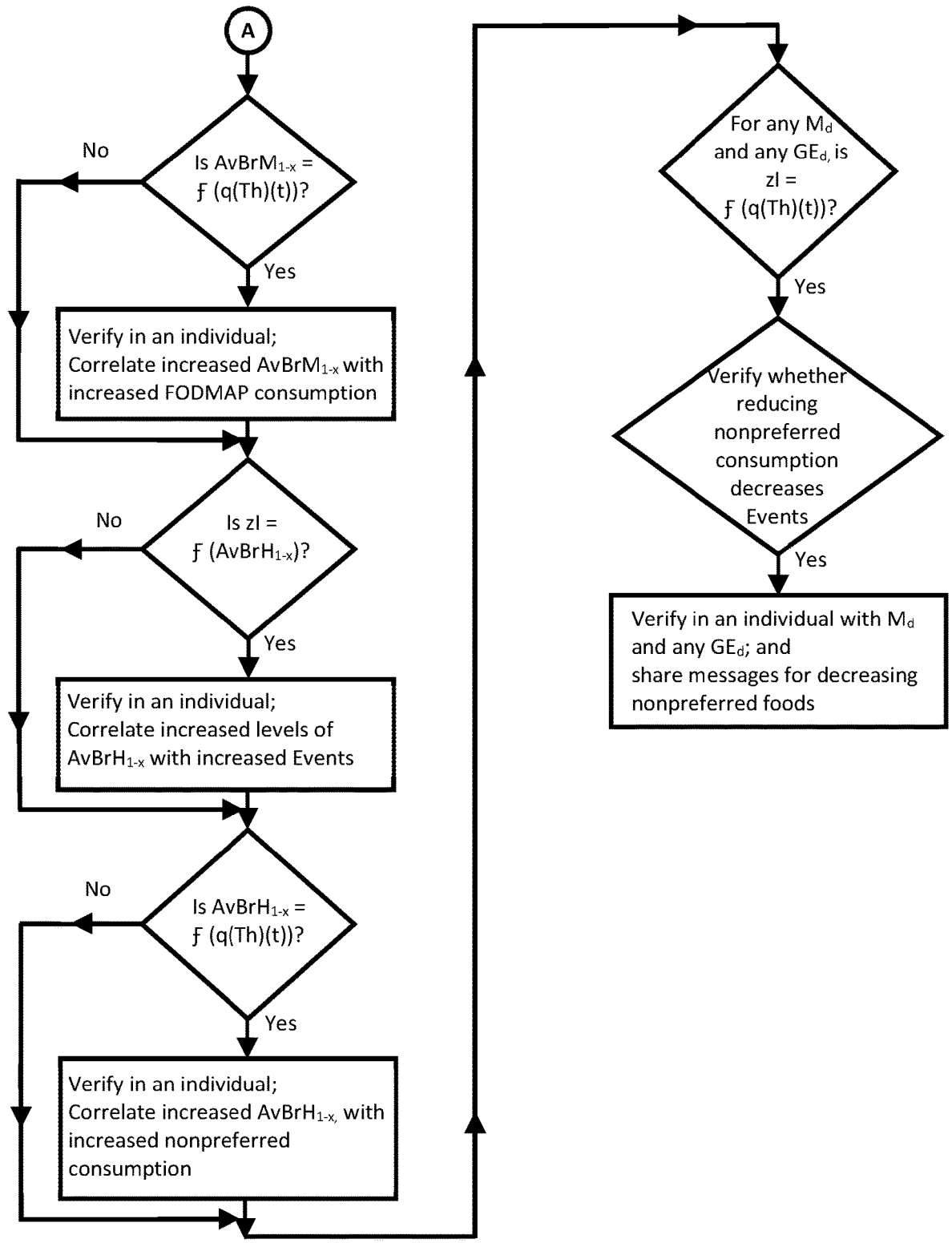

The steps 1-22 above and Figs. FIGS. 5A, 5B provides a rigorous analysis of a number of data points from test subjects, with the objective to provide an optimized diet for an individual with IBD. It shows further, how to construct messages for the individual to adhere to or optimize the diet to reduce symptoms of IBD. FIGS. 6A, 6B summarize steps 1-22 in equation form.

Another set of data points can also be analyzed and then applied to an individual, in addition to those in FIGS. 5A, 5B and steps 1-22 above; as shown in FIGS. 6A, 6B. For the steps in FIGS. 7A, 7B (and the steps in 1a et seq below) it is assumed that the correlation in step 7 above, i.e., zl=f (q(Th)(t)), had been established in test subjects.

Figure 7A:
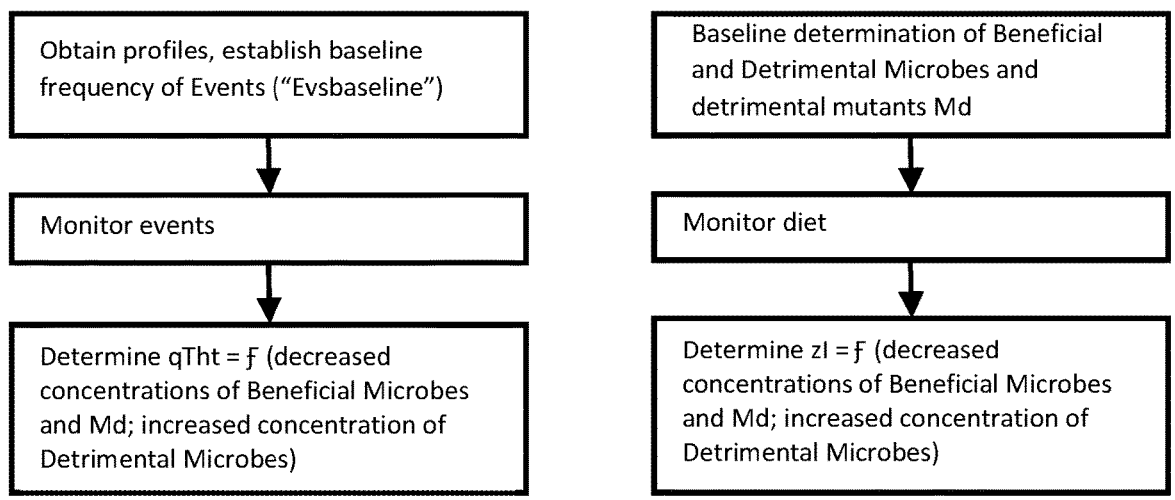
FIG. 7A, 7B are two successive pages of a flow chart showing fecal sample testing for generating preferred gut bacterial composition/microbiome with a low nonpreferred foods and/or low FODMAP diet.
Figure 7B:
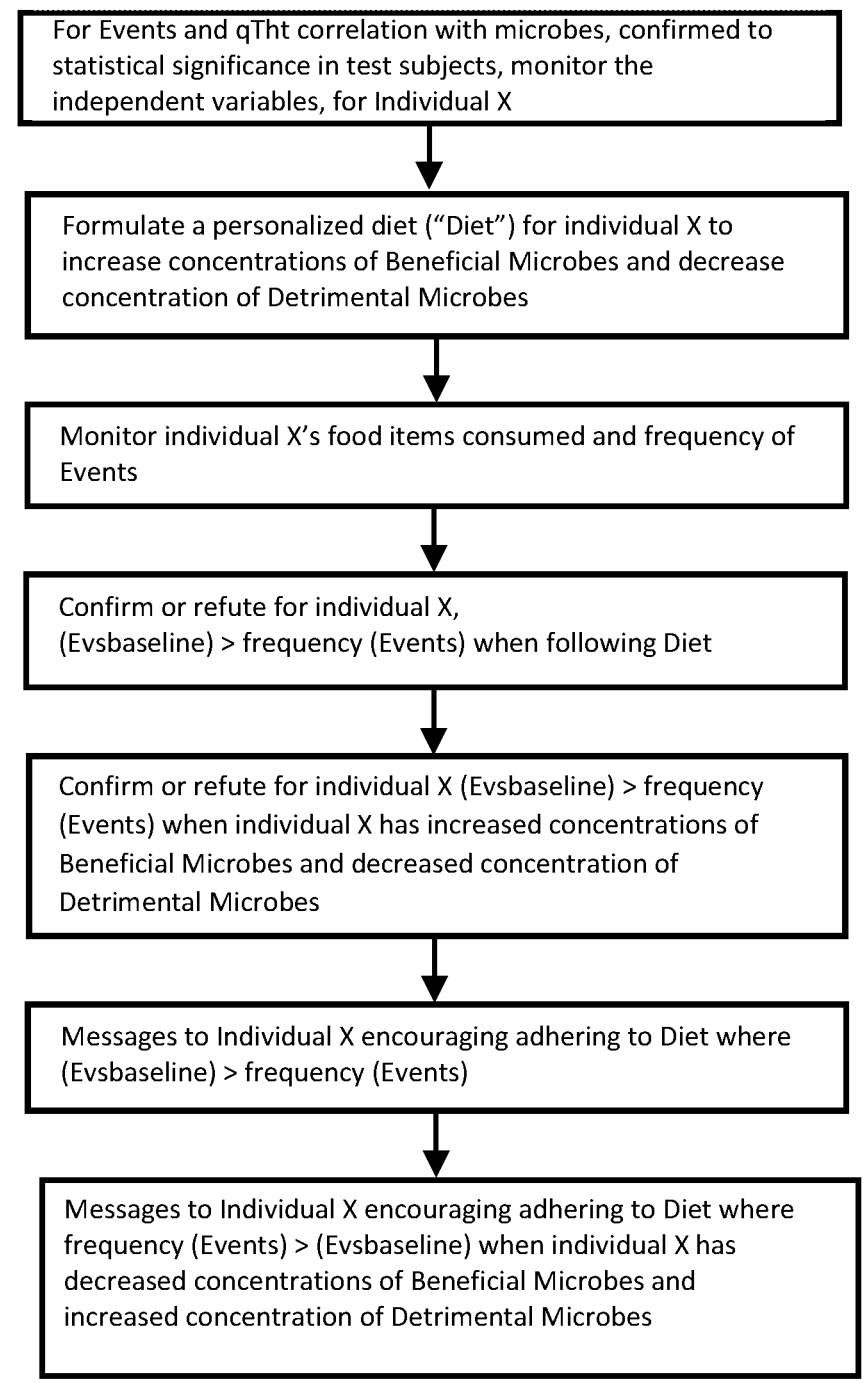

These data points relate to the composition of the gut's bacteria, also known as the microbiome. The full explanation of the flow chart in FIGS. 7A, 7B is as follows in steps 1a to 9a.

1a) Obtain details of digestive health of each test subject: health profiles, and past and present digestive ailments i.e.: whether suffering from IBS, IBD, frequent diarrhea, high frequency flatulence, high frequency bowel movements ("Events" or "symptoms"), and also the baseline frequency of Events, ("Evsbaseline");

2a) Perform baseline fecal sample collection for test subjects to initially determine: (i) concentrations of Bifidobacteria, *Lactobacillus, Faecalibacterium prausnitzii* and Propionibacteriaceae ("Beneficial Microbes"); (ii) concentrations of *Bacteroides fragilis*, Ruminococcaceae and *Clostridium* ("Detrimental Microbes"); and (iii) presence of any mutants of Beneficial Microbes or Detrimental Microbes (based on presence of any Markers1-x) which are associated with Zr (referred to as "Mutants" and including "Md").

3a) Monitor diet of each test subject using a wireless device which allows input of all food items and quantity consumed; with recommendations on screen for low FODMAP foods, and preferably showing carbohydrate content and glycemic Index, fat and protein content, gluten levels, for each meal or for each food item;

4a) Collect fecal samples at intervals for each test subject: and monitor concentrations of Beneficial Microbes and Detrimental Microbes and Mutants, during each collection period;

5a) Use a software agent to determine correlation of qTht with decreased concentrations of Beneficial Microbes and increased concentration of Detrimental Microbes and absence of Mutants; and using a univariate hypothesis test, where the null hypothesis is "qTht is not associated with increased concentrations of Beneficial Microbes and decreased concentration of Detrimental Microbes and absence of Mutants;" at a confidence interval (CI) of at least 95% for the null hypothesis;

6a) Use a software agent to determine correlation of increased frequency of events, zl, with decreased concentrations of Beneficial Microbes and increased concentration of Detrimental Microbes and/or presence of Mutants.

7a) If the correlation in step 5a or 6a is established at a confidence interval (CI) of at least 95% for the null hypothesis, confirm or refute for individual X the correlation between qTht and/or zl with decreased concentrations of Beneficial Microbes and increased concentration of Detrimental Microbes and presence of Mutants;

8a) if the correlation in step 5a is established for individual X, but individual X reports consuming only low FODMAP or other recommended foods and fecal samples do not show increased concentrations of Beneficial Microbes and decreased concentration of Detrimental Microbes and absence of Mutants; send messages to individual X to sequentially eliminate particular foods typically consumed until either all foods consumed are eliminated and deemed not causative, or foods associated with the failure to increase concentrations of Beneficial Microbes and decrease concentration of Detrimental Microbes reduce Mutants are identified; and 9a) If individual X shows increased concentrations of Beneficial Microbes and decreased concentration of Detrimental Microbes when following a low FODMAP or other recommended diet, and shows the opposite when not following a low FODMAP or other recommended diet: message individual X about (i) the importance of consistently following the low FODMAP or other recommended diet and (ii) specifying in the messages how to conform individual X's food intake to the low FODMAP or other recommended diet, based on the food intake reported by individual X.

Essentially the same systems as above and in FIGS. 5A-7B could also be used to identify supplements, prescription drugs, exercise or manipulation regimes, or other treatment methods—instead of or in addition to relying on consuming a low FODMAP diet to reduce Events. To find such other treatment methods, the same steps 1-22 and 1a to 9a above (as shown in the flow charts in FIGS. 5A, 5B and 7A, 7B, respectively) can be performed, but with the "other treatment method" being tested substituted for the "low FODMAP diet." For example, in steps 3 or 3a above, where the treatment tested was a drug, one would monitor each test subject using a wireless device which allows input of the drug dosage consumed. In steps 7 and 5a, one would substitute the drug dosage consumed as the dependent variable. For a drug dosage determined in steps 7 and 8 to minimize Events, that drug dosage can be tested by an individual ("individual X") to determine if it is effective for the individual in reducing Events. The relationship between the drug consumption and the various indicators in step 16, i.e., "gene expression levels<GEd, VOCsLvL<VOCAd, and B-VOCsLvL>VOCBd; AvBrM<BrMd; AvBrH<BrHd" or between the drug consumption and increased concentrations of Beneficial Microbes and decreased concentration of Detrimental Microbes and Mutants in step 5a, can also be determined as additional verification that the drug is effective for reducing Events. A supplement would be tested and verified in the same manner, as could any type of exercise or manipulation regimes, or other treatment methods.

Where the drug, supplement or other treatment method was shown to reduce Events for individual X, they could be messaged to adhere to the treatment when any of the indicators in step 16 or 5a indicated one would expect increased Events.

FIGS. 6A, 6B outline another related embodiment, in equation form, where a genetic marker or gene expression level is determined to predispose test subjects to IBD or Events in test subjects, after going through the steps 1 to 12 above; one can go through steps 13 to 22 above for an individual Y with the marker or gene expression level, and determine if increased frequency of Events is dependent on qTht. The same treatment in steps 21 and 22 can be used, if so. If not, one can substitute a drug, supplement or another therapy for qTht for an individual (individual Y), and if determined to be effective in ameliorating IBD or reducing frequency of Events, perform similar monitoring of individual Y's adherence to the treatment regimen, by monitoring the same indicators as in steps 13 to 20 and/or 5a and 6a. Again, where these indicators indicate individual Y is not adhering to the treatment regime, messages can be sent instructing adherence, and the importance of doing so. Again, the various indicators (like VOCsLvL1-x; B-VOCsLvL1-x; AvBrM; AvBrH) can also serve as a verification of individual Y's adherence to the treatment regime, and whether individual Y is truthfully reporting compliance with the treatment regime. Messages can be sent about the importance of compliance with the treatment regime when the indicators predict an increase in frequency of Events; whether or not such increase is reported by individual Y.

In another related embodiment, it can be determined for an individual (individual Z) if any gene expression levels correlate with a particular diet, or with consumption of any drug, supplement or other therapy, and with increased or reduced frequency of Events. In such case, the gene expression level can be used to monitor compliance by individual Z with the diet or the other treatment regime, as described above.

Another related embodiment is to standardize messaging to test subjects and individuals. The first step in message selection, for querying the subject's condition and for instructing treatment, is establishing, initially, a testing set of messages for each domain, and verifying that the messages are not confusing or ambiguous or difficult to understand and correctly answer. This is accomplished by determining Cronbach's Alphas for a set of messages sent to users. For a quantity which is a sum of K components (also called testlets or items) X=Y1+Y2+Y3 ... YK, Cronbach's alpha is defined as:

$$\alpha = \left(\frac{k}{k-1}\right)\left(1 - \frac{\sum_{i=1}^{k}\sigma_{y_i}^2}{\sigma_x^2}\right)$$

where $\sigma_x^2$ is the variance of the observed total scores from subjects/individuals and where $\sigma_{y_i}^2$ is the variant of component i for the responding subjects/individuals.

To apply Cronbach's alpha in formulating a database of clear questions, for each test subject and user, one compares the sum of items' variance (through the whole set of responses from test subjects and users) to the variance of the sum of the total test scores.

If the sum of items' variance is significantly greater than the variance of the sum of the total test scores, it means that the portion of the errors resulting from misinterpretation, confusion, misunderstanding or related reasons is large, and the status the questions are designed to determine is unreliable. In such cases, the questions need to be reformulated and the new questions need to be tested for reliability using Cronbach's alpha again.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of treating one or more of the conditions of IBS, IBD, frequent diarrhea, high frequency flatulence or high frequency bowel movements by finding an avoidance diet eliminating non-preferred foods to minimize at least one symptom of said conditions and instructing adherence to the avoidance diet by an individual, the method comprising:
   a) finding an avoidance diet by:
      A) assaying fecal samples from a group of test subjects for one or more of: (i) DNA and/or RNA markers associated with the test subjects having the at least one symptom, but not in wild-type, designated Markers1-x; (ii) gene expression of any candidate genes whose expression is elevated or decreased in the test subjects but not in a population which does not exhibit the at least one symptom, designated GeneExp1-x; (iii) concentrations, in samples taken from a subset of the test subjects while they are exhibiting the at least one symptom, of a first set of volatile organic compounds designated VOCsLvL; (iv) concentrations, in samples taken from the subset of test subjects while they are exhibiting the at least one symptom, of a second set of volatile organic compounds designated B-VOCsLvL; and (v) gut concentrations, in samples taken from the subset of test subjects while they are exhibiting the at least one symptom, of one or more of the bacteria: Bifidobacteria, *Lactobacillus, Faecalibacterium prausnitzii*, Propionibacteriaceae, *Bacteroides fragilis*, Ruminococcaceae and *Clostridium*; and/or B) assaying breath samples from the test subjects or gas from the fecal samples while the test subjects are exhibiting the at least one symptom, wherein the assaying determines one or more of: methane levels designated BrM and hydrogen levels designated BrH, wherein BrH and BrM are transmitted to a server when determined from the subjects' breath; and C) identifying a correlation between one or more of Markers1-x, GeneExp1-x, VOCsLvL, B-VOCsLvL, BrM, BrH, gut concentrations of one or more of the bacteria and the at least one symptom in the test subjects; and D) identifying any foods associated with the at least one symptom in the test subjects and designating such foods as non-preferred foods; and E) identifying a correlation between avoidance of certain of the non-preferred foods by the test subjects and one or more of GeneExp1-x, VOCsLvL, B-VOCsLvL, BrM, BrH, and gut concentrations of one or more of the bacteria; and b) determining in the individual if there is a correlation in the individual between avoidance of said certain of the non-preferred foods by the individual and alleviating the at least one symptom in the individual and, if said correlation is established, instructing adherence to the avoidance diet by sending the individual instructions to avoid said certain of the non-preferred foods.

2. The method of claim 1 further including determining in said individual, if there is a correlation between alleviating or worsening at least one symptom and one or more of: Markers1-x, GeneExp1-x, VOCsLvL, B-VOCsLvL, BrM, BrH, and gut concentrations of one or more of the bacteria.

3. The method of claim 1 wherein if one or more of GeneExp1-x, VOCsLvL, B-VOCsLvL, BrM, BrH, and gut concentrations of one or more of the bacteria don't correlate with avoidance of said certain of the non-preferred foods by the individual as in the test subjects, thereby indicating food entry errors by the individual, then the individual is immediately again sent the instructions.

4. The method of claim 3 wherein the individual is sent an instruction to input all food items and quantity consumed.

5. The method of claim 2 further including instructing the individual, when the individual has worsening of the at least one symptom, to sequentially eliminate consumption of particular foods to identify consumed foods which result in failure to alleviate the at least one symptom.

6. The method of claim 3 further including sending the individual a message relating to the importance of consistently avoiding said certain of the non-preferred foods.

7. The method of claim 3 further including sending the individual a message about how to conform the individual's food intake to avoid said certain of the non-preferred foods, based on the food intake reported by the individual during periods when there was lack of alleviation of the at least one symptom.

8. The method of claim 1 wherein said non-preferred foods are low in fermentable sugars.

9. The method of claim 1 wherein the VOCsLvL are selected from the group consisting of: Butanoic acid, ethyl ester; Propanoic acid, methyl ester; 1-Methyl-2-(1-methylethyl)-benzene; Butanoic acid, butyl ester; Butanoic acid, propyl ester; Hexanoic acid, methyl ester; Propanoic acid, propyl ester; Acetic acid, butyl ester; Butanoic acid, 3-methyl-, butyl ester; Propanoic acid, butyl ester; Cyclohexanecarboxylic acid, ethyl ester; Butanoic acid, 2-methyl-, propyl ester; Ethanoic acid, ethyl ester; Pentanoic acid, 4-methyl; Acetic acid, pentyl ester; Pentanoic acid, butyl ester; Butanoic acid, 3-methyl-, propyl ester; Cyclohexanecarboxylic acid, propyl ester; 6-Methyl-5-hepten-2-one; Propanoic acid, 3-methyl-butyl ester; Ethanoic acid, 3-methyl-1-butyl ester; Cyclohexanecarboxylic acid, butyl ester; Benzoic acid, 2-hydroxy-, methyl ester; Pentanoic acid, 4-methyl-, pentyl ester; Butanoic acid, 3-methyl-, methyl ester; Thiopivalic acid; 5-Methyl-2-(1-methylethyl)-cyclohexanone; and 4-Methyl-1-Indole.

10. The method of claim 1 wherein the B-VOCsLvL are selected from the group consisting of: 2-Heptanone; 2-Methylpropanal; 3-Methylbutanoic acid; Undecane; 3-Methylbutanal; 2-Methylpropanoic acid; 2-Methyl-1-propanol; 1R-a-Pinene; 2-Penhifizran; Methoxy-phenyl-oxime; and 2-Methylfuran.

11. The method of claim 1 wherein the VOCsLvL and B-VOCsLvL are determined in gas from the fecal sample.

12. A method of treating one or more of the conditions of IBS, IBD, frequent diarrhea, high frequency flatulence or high frequency bowel movements by finding an avoidance diet eliminating non-preferred foods to minimize at least one symptom of said conditions and instructing adherence to the avoidance diet by an individual, the method comprising:

a) finding an avoidance diet by:

A) assaying fecal samples from a group of test subjects exhibiting the at least one symptom, for one or more of: (i) concentrations of a first set of volatile organic compounds designated VOCsLvL; (ii) concentrations of a second set of volatile organic compounds designated B-VOCsLvL; and (iii) gut concentrations of one or more of the bacteria: Bifidobacteria, *Lactobacillus*, *Faecalibacterium prausnitzii*, Propionibacteriaceae, *Bacteroides fragilis*, Ruminococcaceae and *Clostridium*;

B) assaying breath samples from the test subjects exhibiting the at least one symptom, wherein the assaying determines one or more of: methane levels designated BrM and hydrogen levels designated BrH, wherein BrH and BrM are transmitted to a server;

C) identifying a correlation between one or more of VOCsLvL, B-VOCsLvL, BrM, BrH, gut concentrations of one or more of the bacteria and the at least one symptom in the test subjects;

D) identifying any foods associated with the at least one symptom in the test subjects and designating such foods as non-preferred foods; and E) identifying a correlation between avoidance of certain of the non-preferred foods by the test subjects and one or more of VOCsLvL, B-VOCsLvL, BrM, BrH, and gut concentrations of one or more of the bacteria; and b) determining in the individual if there is a first correlation in the individual between avoidance of said certain of the non-preferred foods by the individual and alleviating the at least one symptom in the individual and determining in said individual, if there is a second correlation between alleviating or worsening of the at least one symptom and one or more of: VOCsLvL, B-VOCsLvL, BrM, BrH, and gut concentrations of one or more of the bacteria; and if said first or second correlation is established, instructing adherence to the avoidance diet by sending the individual instructions to avoid said certain of the non-preferred foods.

13. The method of claim 12 wherein if one or more of VOCsLvL, B-VOCsLvL, BrM, BrH and gut concentrations of one or more of the bacteria don't correlate with avoidance of said certain of the non-preferred foods by the individual as in the test subjects, thereby indicating food entry errors by the individual, then the individual is immediately again sent the instructions.

14. The method of claim 13 wherein the individual is sent an instruction to input all food items and quantity consumed.

15. The method of claim 12 further including instructing the individual, when the individual has worsening of at least one symptom, to sequentially eliminate consumption of particular foods to identify consumed foods which result in failure to alleviate the at least one symptom.

16. A method of treating one or more of the conditions of IBS, IBD, frequent diarrhea, high frequency flatulence or high frequency bowel movements by finding an avoidance diet eliminating non-preferred foods to minimize at least one symptom of said conditions and instructing adherence to the avoidance diet by an individual, the method comprising:
   a) finding an avoidance diet by:
      A) assaying fecal samples from a group of test subjects exhibiting the at least one symptom wherein the assaying determines: (i) concentrations of one or more of the beneficial bacteria: Bifidobacteria, *Lactobacillus, Faecalibacterium prausnitzii*, Propionibacteriaceae and (ii) concentrations of one or more of the detrimental bacteria: *Bacteroides fragilis*, Ruminococcaceae and *Clostridium;*
      B) identifying a correlation between the concentrations of one or more of the beneficial or detrimental bacteria and the at least one symptom in the test subjects;
      C) identifying foods associated with the at least one symptom in the test subjects and designating such foods as non-preferred foods; and
      D) identifying a correlation between the concentrations of one or more of the beneficial or detrimental bacteria and avoidance of certain of the non-preferred foods by the test subjects; and
   b) determining if there is a first correlation in the individual between avoidance of said certain of the non-preferred foods by the individual and alleviating the at least one symptom in the individual; and determining, in said individual, if there is a second correlation in said individual between concentrations of one or more of the beneficial or detrimental bacteria and alleviating or worsening of the at least one symptom in the individual; and, if said first or second correlation is established, instructing adherence to the avoidance diet by sending the individual instructions to avoid said certain of the non-preferred foods.

17. The method of claim 16 wherein if concentrations of one or more of the beneficial or detrimental bacteria don't correlate with avoidance of said certain of the non-preferred foods by the individual as in the test subjects, thereby indicating food entry errors by the individual, then the individual is immediately again sent the instructions.

18. The method of claim 17 wherein the individual is sent an instruction to input all food items and quantity consumed.

19. The method of claim 16 further including instructing the individual, when the individual has worsening of the at least one symptom, to sequentially eliminate consumption of particular foods to identify consumed foods which result in failure to alleviate the at least one symptom.

20. The method of claim 16 further including sending the individual a message about how to conform the individual's food intake to avoid said certain of the non-preferred foods, based on the food intake reported by the individual during periods when there was lack of alleviation of the at least one symptom.

* * * * *